United States Patent [19]
Bajada

[11] Patent Number: 5,478,348
[45] Date of Patent: Dec. 26, 1995

[54] MEDICAL SHARP APPARATUS WITH MEANS FOR RENDERING IT SAFE AFTER USE

[76] Inventor: Serge Bajada, 221 High Street, Fremantle, Australia, 6160

[21] Appl. No.: 218,241

[22] Filed: Mar. 28, 1994

[30] Foreign Application Priority Data

Sep. 3, 1993 [AU] Australia .................... PM1008

[51] Int. Cl.⁶ .................................................. A61B 17/32
[52] U.S. Cl. ............................................ 606/185; 606/172
[58] Field of Search .................................. 606/170, 172, 606/185

[56] References Cited

U.S. PATENT DOCUMENTS

| | | | |
|---|---|---|---|
| 3,945,117 | 3/1976 | Beaver | 606/17 X |
| 4,516,575 | 5/1985 | Gerhard et al. | 606/172 X |
| 4,534,348 | 8/1985 | Fedorov et al. | 606/172 X |
| 4,580,564 | 4/1986 | Andersen | 606/172 |
| 4,738,255 | 4/1988 | Goble et al. | 606/232 X |
| 4,738,261 | 4/1988 | Enstrom | 606/172 X |
| 5,314,417 | 5/1994 | Stephens et al. | 606/170 X |
| 5,324,288 | 6/1994 | Billings et al. | 606/172 X |

FOREIGN PATENT DOCUMENTS 589243 11/1988 Australia .

Primary Examiner—Stephen C. Pellegrino
Assistant Examiner—Nancy Mulcare
Attorney, Agent, or Firm—Stephen C. Glazier

[57] ABSTRACT

A single use medical sharp device includes an outer sheath and a shank disposed in the sheath. The shank has a leading pointed end and a trailing handle end. The shank and the sheath are inter-engaged so that the shank has an extended operational position and a retracted safe position.

8 Claims, 5 Drawing Sheets

MEDICAL SHARP APPARATUS WITH MEANS FOR RENDERING IT SAFE AFTER USE

BACKGROUND OF THE INVENTION

The present invention relates to a medical sharp apparatus with means for rendering it safe after use.

The present invention is described herein with particular reference to apparatus for testing the sensory system in human or animals by means of pins, but it is to be noted that the present invention is of general applicability to any form of medical sharp apparatus which is used for any purpose, which needs safe disposal after use.

It is known to use pins to test the sensory system in humans or animals. However, there is a risk of a pin being used on more than one subject unless suitable precautions are taken. If a pin is used on more than one subject there may be a risk of cross-infection. Thus, there is a need for a means for providing pins for use in testing the sensory system in humans or animals by which the risk of one pin being used on more than on subject is reduced. In Australian Patent No. 589243, by the same inventor as the present invention, there is described and claimed an effective multiple use apparatus for testing the sensory system in humans and animals in which the possibility of a pin being used on more than one subject is considerably reduced. However, it has now been discovered that with medical sharps such as sensory testing pins there is an advantage to be gained from using an apparatus designed to be discarded after being used on a single patient. This mode of operation is more familiar to some medical practitioners and requires less of a change of style of operation compared with multiple use devices. Even with such a device, however, it is highly desirable to be able to render it safe before disposal.

SUMMARY OF THE INVENTION

The present invention provides a single use medical sharp apparatus which is arranged to be rendered salt immediately after use at the site of use before disposal. In accordance with one aspect of the present invention there is provided a single use medical sharp comprising an outer sheath and a shank disposed in the sheath, wherein the sheath and the shank have interengagement means in the form of a projection on one member arranged to engage with a recess on the other member, there being provided a first channel which is engageable in the first instance with the projection, a second channel, and a third channel which interconnects the first and second channels, the second channel being engageable with the projection only via the third channel from the first channel and being arranged so that the shank has an extended operational position and a retracted safe position after use.

Preferably, the shank also has an intermediate pre-use position when in engagement with the second channel. The shank may be part of a sensory testing pin having a leading pointed end and a trailing handle end. Alternatively, the shank may be any medical sharp whose function is to penetrate the body.

DESCRIPTION OF THE PREFERRED EMBODIMENTS

Figure 1:
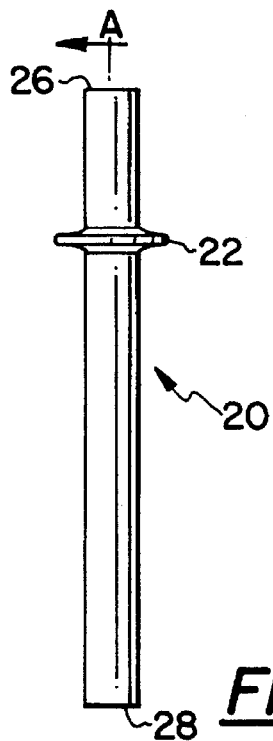
FIG. 1 is a side elevation of a sheath of the apparatus of the present invention in upright orientation.
Figure 2:
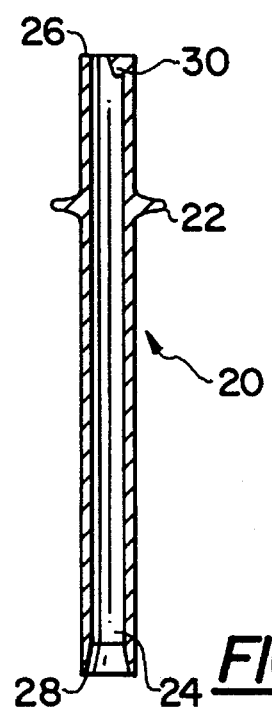
FIG. 2 is a section along the line A—A of FIG. 1.
Figure 3:
FIG. 3 is a view to an enlarged scale of one end of the sheath of FIG. 1 in section as shown in FIG. 2.
Figure 3:
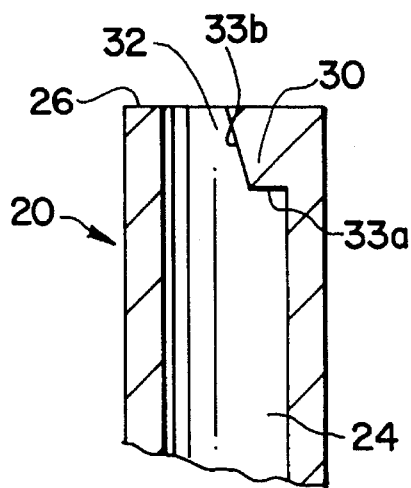
Figure 4:
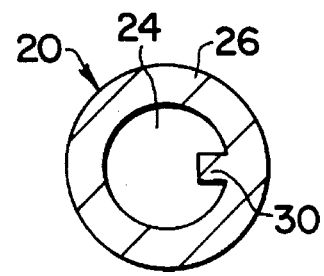
FIG. 4 is a plan view of the sheath of FIG. 1.
Figure 5:
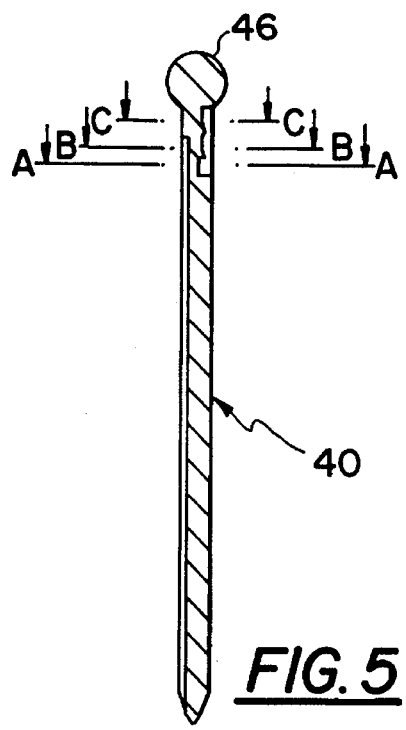
FIG. 5 is a longitudinal sectional view through a pin intended for use with the sheath FIGS. 1 to 4.

In FIGS. 1 to 4, there is shown a sheath 20 having an intermediately located circumferential rib 22 extending around its periphery. As can be seen in FIG. 2, the sheath 20 is hollow and has a longitudinally extending bore 24.

The sheath 20 has a first end 26 and a second end 28. Adjacent the first end 26 the sheath is provided with an inwardly extending projection 30. As can best be seen in FIG. 3, the projection 30 has an innermost wall 32 which is disposed at an angle to the bore 24 such that the inner end of the wall 32 has relatively short face 33a and is closer to the wall of the bore 24 than the outer end of the wall 32 which has a relatively long face 33b. In FIGS. 5 to 11, there is shown a pin 40 having a shank 42 with a first end provided with a point 44 and a second end provided with a handle 46. The pin 40 has a first longitudinally extending slot 48 which can be seen in FIG. 7 and which extends from the point 44 to a region adjacent the handle 46.

Figure 6:
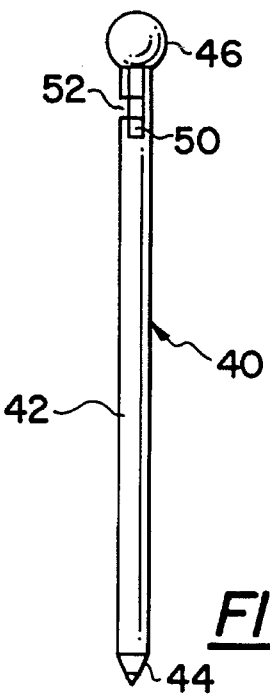
FIG. 6 is a side elevation of the pin of FIG. 5 from one side.
Figure 7:
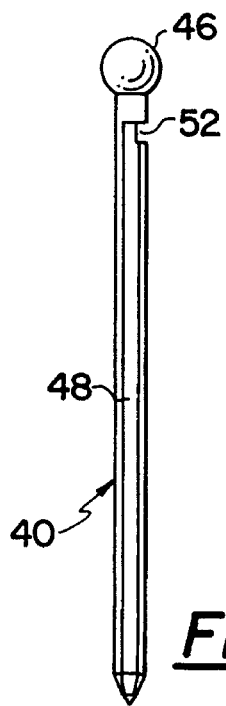
FIG. 7 is a side elevation of the pin of FIG. 5 from another side.

The pin 40 has a second longitudinally extending slot 50 which can be seen in FIG. 6 and which extends from the handle 46 to a point overlapping with the adjacent end of the slot 48. Further, there is a third slot 52 which extends transversely and interconnects the slots 48 and 50 and which can be seen in FIGS. 6 and 7.

Figure 8:
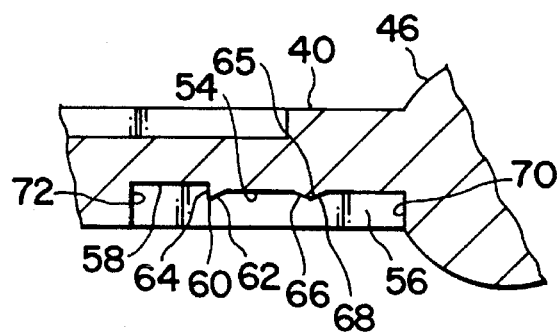
FIG. 8 is a view to an enlarged scale of a slot of the pin of FIG. 5.

As can best be seen in FIG. 8, the slot 50 comprises three regions 54, 56 and 58. The first region 54 is an intermediate region which is in alignment with the slot 52. The region 54 has longitudinal extremities which are bounded by steps. A first step 60 at the longitudinal end remote from the handle 46 has a gently sloping face 62 at the side thereof adjacent to the zone 54 and a substantially vertical face 64 remote from the zone 54. A second step 65 at the longitudinal end adjacent to the handle 46 has gently sloping faces 66 and 68 at both sides thereof.

The region 56 is adjacent to the handle 46 and has an outer end bound by a face 70 at the handle and an inner end bound by the aforementioned sloping face 68.

Figure 9:
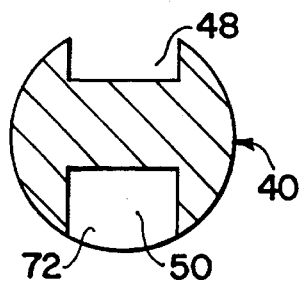
FIG. 9 is a transverse sectional view along the line A—A of FIG. 5.

The region 58 is remote from the handle 46 and has an outer end bounded by the aforementioned face 64 and an inner end bounded by a further substantially vertical face 72 which extends the full width of the pin 40 as an be seen in FIG. 9.

Figure 10:
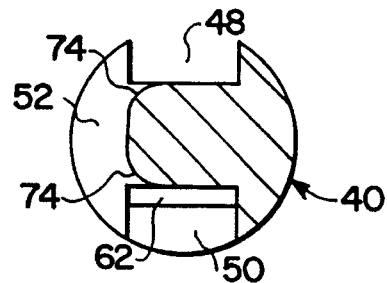
FIG. 10 is a transverse sectional view along line B—B of FIG. 5.
Figure 11:
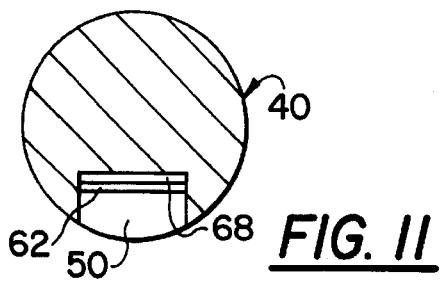
FIG. 11 is a transverse sectional view along the C—C of FIG. 5.
Figure 12:
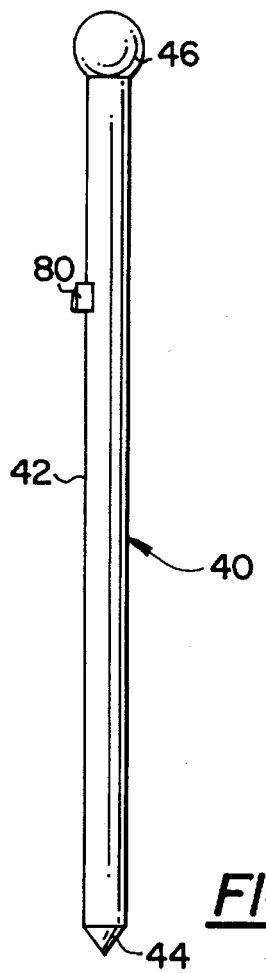
FIG. 12 is a side elevation of an alternative embodiment of a pin in accordance with the present invention.
Figure 13:
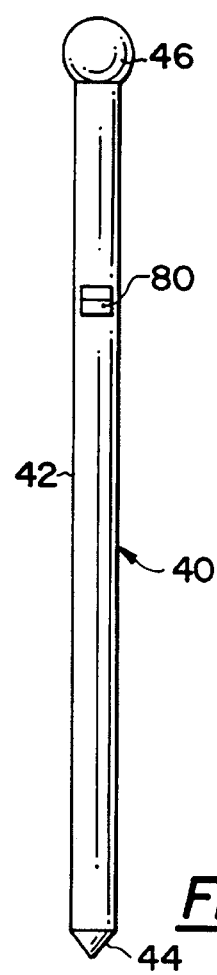
FIG. 13 is a view similar to FIG. 12 from another orientation.

As can be seen in FIG. 10 the transverse slot 52 has rounded ends 74 to facilitate rotation of the pin 40 within the sheath 20 when the projection 30 is in alignment with the slot 52 as will be described.

In use, the pin 40 is inserted into the bore 24 of the sheath 20 with the point 44 leading and the slot 48 aligned with the projection 30. The slot 48 engages with the projection 30 and the insertion of the pin 40 is continued until the projection 30 is in alignment with the transverse slot 52. The pin 40 is then rotated through 180° so that the slot 52 transverses the projection 30. The shape of the floor of the slot 52 with the rounded ends 74 is such that this operation requires slight deformation of the projection 30 to effect the traversing movement through the slot 52. In this way, once rotated, the pin 40 cannot position in the slot 48.

After transversing the slot 52, the projection 30 comes into engagement with the slot 50 at the region 54 thereof. In this position, the pin is located in the sheath 20 in such manner that the point 44 is located within the sheath 20 and the handle 46 is spaced from the sheath 20. In this condition, the pin 40 is available to be activated for use but the point 44 is shielded by the sheath 20.

When it is desired to use the pin 40, the handle 46 is depressed towards the sheath 20, and the step 65 formed by the sloping faces 66 and 68 rides over the projection 30 of the slot 50. In this position, the point 44 projects from the sheath 20 and an operator can use the point for sensory testing by gripping the handle 46 and rib 22. The engagement of the projection 30 in the region 56 also reduces the possibility of the pin 40 being inadvertently moved from its activated position.

When the pin 40 has been used on a single patient, it can be rendered safe by retracting the pin 40 in sheath 20 so that the projection 30 moves out of the region 56 back into the region 54 and then into the region 58. As can be seen in FIG. 8, the region 58 is deeper than the regions 54 and 56 and has the faces 64 at its outer end. Also, the projection 30 has its long face 33b adjacent the face 64. Thus, the pin 40 cannot be removed from engagement of the projection 30 with the region 58 under normal operation conditions. In this deactivated position, the point 44 is within the sheath 20 and not readily accessible and the projection 30 engaging with the region 58 prevents any further longitudinal or rotational movement of the pin 40 relative to the sheath 20.

Figure 14:
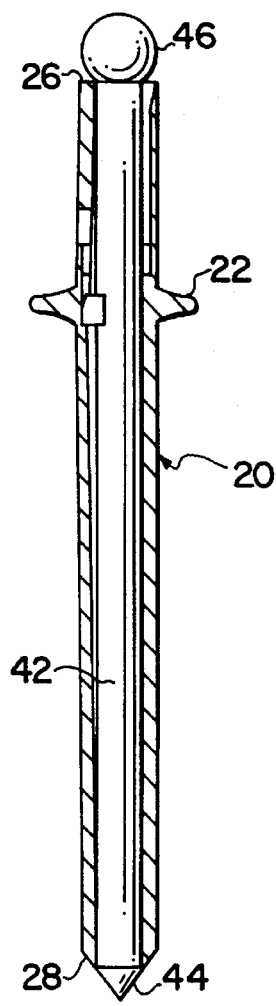
FIGS. 14 is a longitudinal section through an alternative embodiment of sheath in accordance with the present invention containing a pin of FIGS. 12 and 13 in operational condition.
Figure 14A:
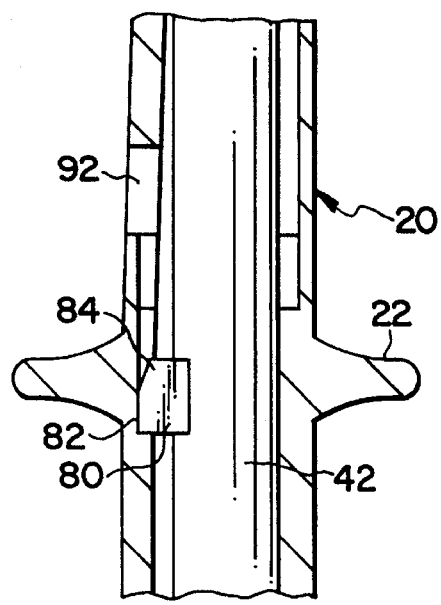
FIG. 14a is a view to an enlarged scale of part of the apparatus of FIG. 14.
Figure 15:
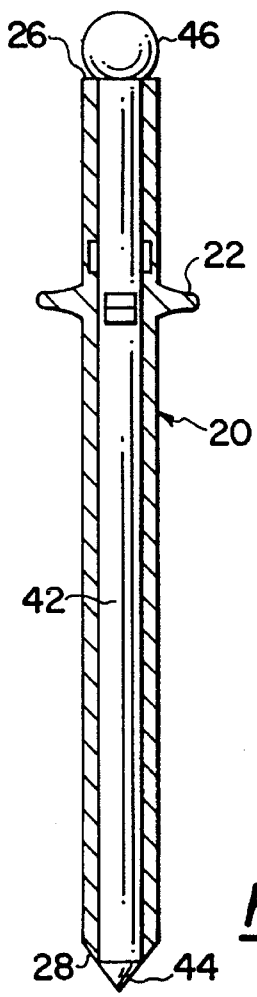
FIG. 15 is a view similar to FIG. 14 from another orientation.

In FIGS. 12 to 17 there is shown an apparatus comprising a pin and a sheath which is similar to that shown in FIGS. 1 to 11 and like reference numerals denote like parts. However, in this case, a projection 80 is mounted to the shank 42 at a point spaced from the handle 46. As can best be seen in FIGS. 14a and 16a, the projection 80 has an outer surface 82 with a chamfered portion 84 at the end thereof closest to the handle 46.

Figure 17:
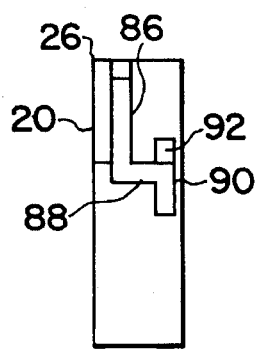
FIGS. 17–19 are schematic views of part of the interior of the sheath of FIGS. 14 to 16 showing configurations of slots formed therein.
Figure 18:
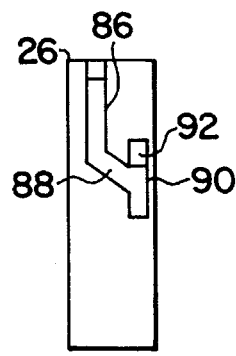
Figure 19:
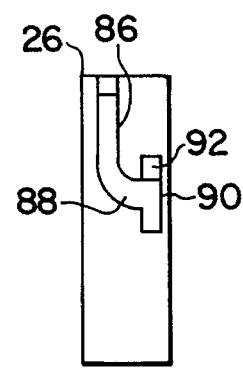

Further, the interior of the sheath 20 is provided with a series of internal slots as shown in FIG. 17. FIGS. 18 and 19 show alternative slot constructions. There is a first slot 86 which extends longitudinally from the end 26. There is a second slot 88 which extends transversely from the slot 86, and a third slot 90 which extends longitudinally and meets with the slot 88 at an intermediate point of the slot 90. In addition, the slot 90 has a trailing portion closest to the handle 46 which contains an aperture 92 which extends right through the thickness of the sheath 20.

In use, the pin 40 is oriented with point 44 foremost so that it can be inserted in the sheath 20 in such manner that the projection 80 can enter the slot 86. When the projection 80 reaches the leading end of the slot 86, the pin 40 is rotated so that the projection 80 enters the slot 88. Upon continued rotation, the projection 80 enters the slot 90 at which position the pin 40 is arranged to be activated. In this position, the projection 80 is located in an intermediate position in the slot 90 and the point 44 is located within the sheath 20. To activate the pin 40, the handle 46 is depressed and the projection 80 moves forward in the slot 90 to stop 94 as can best be seen in FIG. 14 and 14a. At this position, the pin 40 is fixed in position by deformation of the material of the sheath 20 by the projection 80.

When the pin has been used on one patient, it is rendered safe by retracting the handle 46, so as to withdraw the point 44 into the sheath 20. This action is continued until the projection 80 engages with the aperture 92 as can best be seen in FIGS. 16 and 16a.

Figure 16:
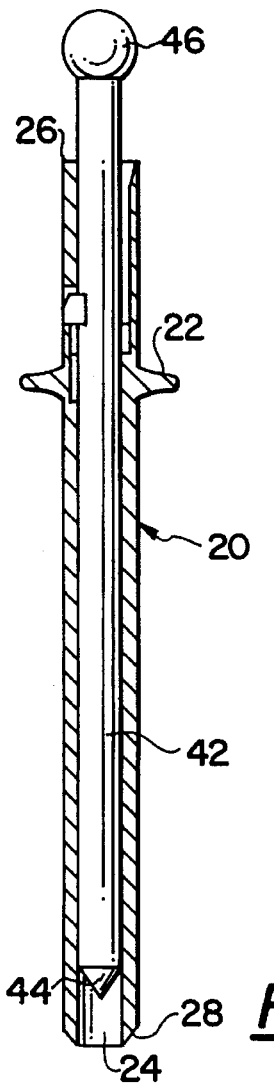
FIG. 16 is a view similar to FIG. 14 showing the pin in retracted condition after use.
Figure 16A:
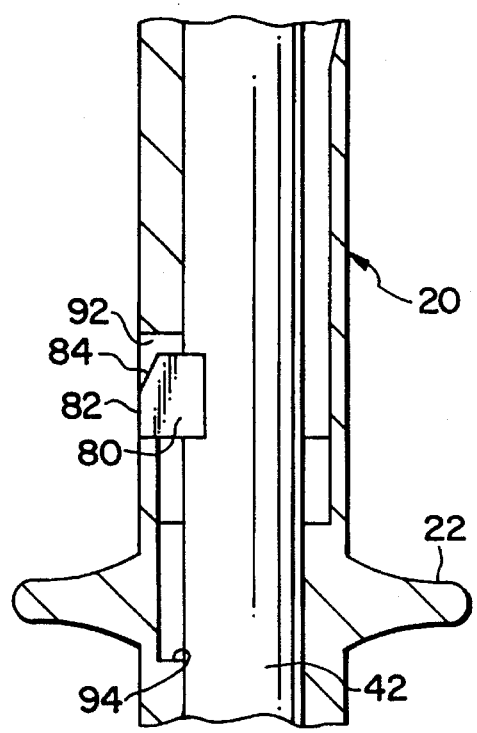
FIG. 16a is a view to an enlarged scale of part of the apparatus of FIG. 16.

As the projection 80 has faces projecting substantially vertically from the shank 42, it is not possible under normal circumstances to disengage the projection 80 from the aperture 92 so that the pin 40 cannot be moved again either longitudinally or in rotation. Also, as shown in FIG. 16 the point 44 is located inside the sheath 20 and is not readily accessible.

The apparatus of the present invention may be conveniently made from plastic material.

The embodiments illustrated and discussed in this specification are intended only to teach those skilled in the art the best way known by the inventor to make and use this invention. Nothing in this specification should be considered as limiting the scope of the present invention. Many changes can be made by those skilled in the art to produce equivalent devices without departing from the invention. The present invention should be limited only by the following claims and their legal equivalents.

For example, it is envisaged that the first and second channels are interconnected by a diagonal or spiral pathway or any other convenient pathway. Various shapes of pathways can be used. Furthermore, the medical sharp in the preferred embodiment discussed herein is a pin, but any other sharp implement can be used, such as for example, a needle, a wire, an electrode, a scalpel, a knife, scissors, or other sharp devices. Likewise, the present invention can be used for any use for the sharp device incorporated into a given embodiment, and this invention is not limited to any particular use for a sharp, such as the testing of sensory systems that is discussed herein.

I claim:

1. A single use medical sharp device, comprising:

an outer sheath, a shank disposed in the outer sheath, the shank having a leading pointed end and a trailing handle end, one of said outer sheath and said shank including a pair of substantially longitudinally extending slots and a transversely extending slot interconnecting said pair of substantially longitudinally extending slots, and a projection defined on the other of said outer sheath and said shank and receivable in each of the substantially longitudinally and transversely extending slots, the shank and the sheath being inter-engaged by said projection and said substantially longitudinally and transversely extending slots so that the shank has an extended operational position and a retracted safe position.

2. The device defined in claim 1, wherein one of the pair of substantially longitudinally extending slots is engageable with the projection only via the transversely extending slot from the other of the pair of substantially longitudinally extending slots, the slots being arranged so that the shank has the extended operational position when the projection is in engagement with the other of the pair of substantially longitudinally extending slots, the retracted safe position when the projection is in engagement with the one of the pair of substantially longitudinally extending slots, and a pre-use position when the projection is in engagement with the one of the pair of substantially longitudinally extending slots.

3. The device defined in claim 2, wherein the one of the pair of substantially longitudinally extending slots includes:

(a) a first location arranged so that the shank is in a pre-use position when the projection is engaged with the one of the pair of substantially longitudinally extending slots at the first location, (b) a first restraining means for restraining the projection in the first location, (c) a second location arranged so that the shank is in a retracted safe position when the projection is engaged with the one of the pair of substantially longitudinally extending slots at the second location, and (d) a second restraining means for restraining the projection in the second location.

4. The device defined in claim 3, wherein the first restraining means includes one of a step and a hole from which the projection can be easily unrestrained.

5. The device defined in claim 3, wherein the second restraining means includes one of a step and a hole from which the projection can not be easily unrestrained.

6. The device defined in claim 1, wherein the shank is locked in said retracted safe position so that it cannot be moved.

7. The device defined in claim 1, wherein said transversely extending slot defines a diagonal pathway.

8. The device defined in claim 1, wherein said transversely extending slot defines a spiral pathway.

\* \* \* \* \*